United States Patent
Suzuki et al.

(10) Patent No.: US 9,150,989 B2
(45) Date of Patent: Oct. 6, 2015

(54) SPUNBONDED NON-WOVEN FABRIC, PRODUCTION PROCESS FOR THE FABRIC AND USE THEREOF

(75) Inventors: Kenichi Suzuki, Ichihara (JP); Tetsuya Yokoyama, Yokkaichi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 343 days.

(21) Appl. No.: 13/640,981

(22) PCT Filed: Apr. 15, 2011

(86) PCT No.: PCT/JP2011/059379
§ 371 (c)(1),
(2), (4) Date: Oct. 12, 2012

(87) PCT Pub. No.: WO2011/129433
PCT Pub. Date: Oct. 20, 2011

(65) Prior Publication Data
US 2013/0035015 A1 Feb. 7, 2013

(30) Foreign Application Priority Data

Apr. 15, 2010 (JP) ................................. 2010-094116
Apr. 15, 2010 (JP) ................................. 2010-094117

(51) Int. Cl.
*D04H 3/153* (2012.01)
*A61F 13/514* (2006.01)
(Continued)

(52) U.S. Cl.
CPC ............ *D04H 3/153* (2013.01); *A61F 13/4902* (2013.01); *A61F 13/514* (2013.01); *D04H 3/005* (2013.01); *Y10T 442/602* (2015.04); *Y10T 442/681* (2015.04)

(58) Field of Classification Search
CPC .... D04H 3/005; D04H 3/153; Y10T 442/602; Y10T 442/681; A61F 13/514; A61F 13/4902
USPC .......................................... 442/328, 401, 415
See application file for complete search history.

(56) References Cited

U.S. PATENT DOCUMENTS 5,118,780 A * 6/1992 Hirai et al. ...................... 528/83
5,470,639 A 11/1995 Gessner et al.
(Continued)

FOREIGN PATENT DOCUMENTS

| JP | 03-265620 A | 11/1991 |
| JP | 07-503502 A | 4/1995 |

(Continued)

OTHER PUBLICATIONS

Examination Report (Office Action) dated Jul. 23, 2014, issued by the European Patent Office in the corresponding European Application No. 11768954.7. (5 pages).
(Continued)

*Primary Examiner* — Jeremy R Pierce
(74) *Attorney, Agent, or Firm* — Buchanan, Ingersoll & Rooney PC

(57) ABSTRACT

The present invention provides a spunbonded non-woven fabric having excellent productivity, stretchability, touch and fuzz resistance without adhesion thereof on a roll and the like just after fiber deposition during the production. The spunbonded non-woven fabric comprises long fibers of a thermoplastic polyurethane elastomer (A) containing ethylene bisoleic acid amide and/or crosslinked organic fine particles and having a hardness of 75 to 85, and the spunbonded non-woven fabric comprises the long fibers of the thermoplastic polyurethane elastomer (A) and long fibers of a thermoplastic resin (B) other than the thermoplastic polyurethane elastomer (A). The present invention also provides uses thereof.

12 Claims, 1 Drawing Sheet

(51) Int. Cl.
*D04H 3/005* (2012.01)
*A61F 13/49* (2006.01)

(56) References Cited

U.S. PATENT DOCUMENTS

| | | | |
|---|---|---|---|
| 5,807,796 A * | 9/1998 | Degrand et al. | 442/401 |
| 5,925,697 A | 7/1999 | Bräuer et al. | |
| 5,997,989 A | 12/1999 | Gessner et al. | |
| 6,477,926 B1 | 11/2002 | Swisher et al. | |
| 2004/0154731 A1 | 8/2004 | Sommer et al. | |
| 2006/0121812 A1 | 6/2006 | Suzuki et al. | |
| 2006/0141883 A1 | 6/2006 | Nishiguchi et al. | |
| 2008/0233819 A1 * | 9/2008 | Tsujiyama et al. | 442/329 |
| 2008/0264550 A1 | 10/2008 | Sommer et al. | |
| 2010/0092710 A1 * | 4/2010 | Welker et al. | 428/36.9 |
| 2010/0248575 A1 | 9/2010 | Malz | |

FOREIGN PATENT DOCUMENTS

| | | |
|---|---|---|
| JP | 09-241500 A | 9/1997 |
| JP | 2000-297210 A | 10/2000 |
| JP | 2004-197291 A | 7/2004 |
| JP | 2004-244791 A | 9/2004 |
| JP | 2004-244793 A | 9/2004 |
| JP | 2005-029907 A | 2/2005 |
| JP | 2006-274000 A | 10/2006 |
| JP | 2008-213284 A | 9/2008 |
| JP | 2008-260906 A | 10/2008 |
| JP | 2010-509512 A | 3/2010 |

OTHER PUBLICATIONS

International Search Report (PCT/ISA/210) issued on Jun. 28, 2011, by the Japanese Patent Office as the International Searching Authority for International Application No. PCT/JP2011/059379.

* cited by examiner

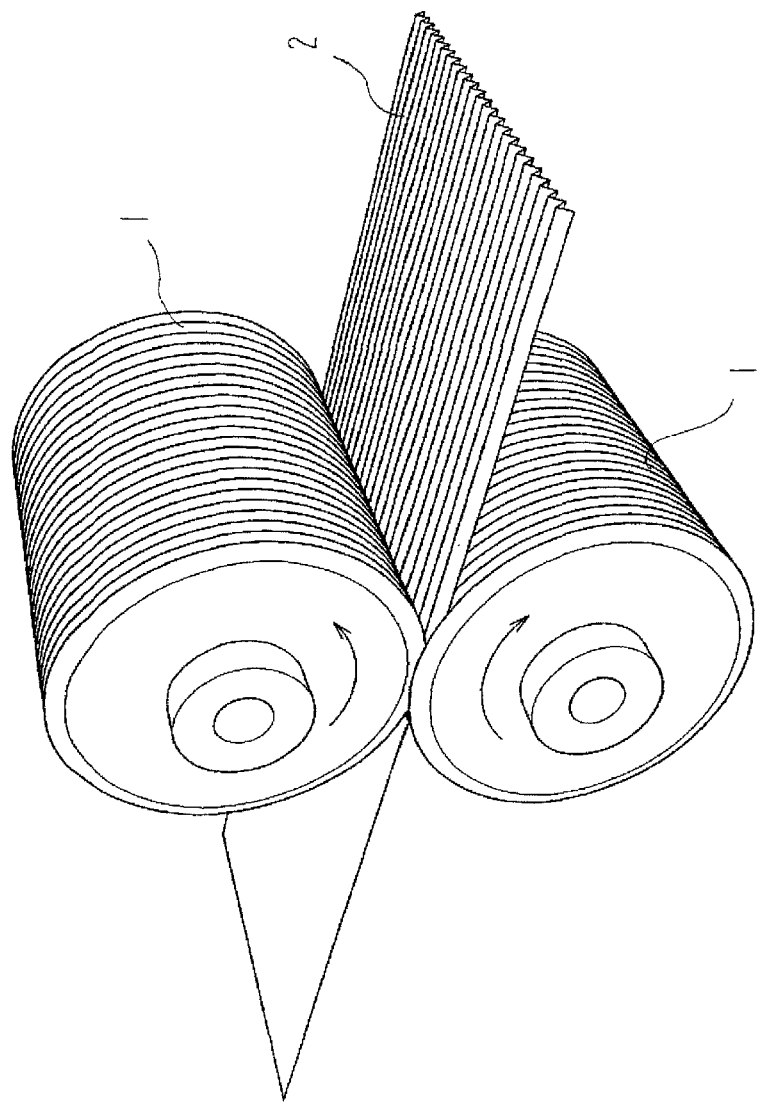

SPUNBONDED NON-WOVEN FABRIC, PRODUCTION PROCESS FOR THE FABRIC AND USE THEREOF

TECHNICAL FIELD

The present invention relates to a spunbonded non-woven fabric which comprises long fibers comprising a thermoplastic polyurethane elastomer having a low hardness, specifically it relates to a spunbonded non-woven fabric which comprises long fibers comprising a thermoplastic polyurethane elastomer having a low hardness and long fibers comprising a thermoplastic polymer other than the above thermoplastic polyurethane elastomer. The present invention further relates to a laminate containing the spunbonded non-woven fabric and to sanitary materials obtainable by using the same.

TECHNICAL BACKGROUND

In recent years, non-woven fabrics are used widely for various kinds of uses because of having excellent permeability and flexibility. On this account, non-woven fabrics are required to have various properties according to their uses and the properties are required to be further improved.

For example, non-woven fabrics used for sanitary materials such as paper diapers, sanitary napkins and the like, and base fabric such as wet compress pack materials and the like are required to have water resistance and excellent moisture permeability. Furthermore, the non-woven fabrics are required to have stretchability and bulk properties according to a portion for use.

Examples of a method of adding stretchability to the non-woven fabrics are a method of using a thermoplastic elastomer as a material for a spunbonded non-woven fabric (referred to Patent document 1), a method of using mixed fibers which comprise fibers made of a polymer containing a thermoplastic polyurethane elastomer and fibers made of a thermoplastic polymer other than the thermoplastic polyurethane elastomer as fibers for forming a non-woven fabric (referred to Patent document 2). Moreover, differing to the addition of stretchability, a long fiber non-woven fabric obtainable by combining adhesive fibers made of a hydrogenated styrene block copolymer and non-adhesive fibers and the like are variously proposed (referred to Patent document 3).

Mixing the fibers made of the thermoplastic polyurethane elastomer, stretchability is added. Moreover, stretchability (elastic recovery properties) is desired according to the use. As a method of increasing stretchability, there is a method of using a thermoplastic polyurethane elastomer having a low hardness and excellent elastic recovery properties.

However, a thermoplastic polyurethane elastomer having a low hardness is soft. In producing a spunbonded non-woven fabric by mixing fibers made of a thermoplastic polyurethane elastomer having a low hardness, the fibers prepared just after deposition are easily deformed by a rotational device that a linear pressure is applied on the deposited fibers such as calendar roller (for example, referred to Patent document 4), or a conveyer, and thereby the contact area is increased. In the case that fusion bonding of the fibers is insufficient, there is a possibility that the fibers adhere to the rotational device and the insufficient fusion bonding has an industrial problem.

For example, in a process that a web which comprises only long fibers made of a thermoplastic polyurethane elastomer, prepared by a spun bonding method are fusion bonded each other completely or no completely and unified in the step of contacting the web with a rotational device, since a force of generating a peeling force higher than an adhesion force functions in a mechanical direction, fusion bonding is hard to be caused. In the case of producing a spunbonded non-woven fabric which comprises long fibers made of a thermoplastic polyurethane elastomer and long fibers made of a thermoplastic polymer other than the thermoplastic polyurethane elastomer, the fibers are hardly fusion bonded each other in the step of collecting the fibers on a conveyor after opening, and heterogeneous fibers are only deposited and the web is not unified. When the web is contacted with a rotational device such as a calendar roller and the like, the long fibers made of a thermoplastic polyurethane elastomer are adhered on the rotational device at the beginning and the whole web is frequently wound around the rotational device in the end. The production has an industrial problem.

In a process of using mixed fibers which comprise fibers made of a polymer containing a thermoplastic polyurethane elastomer and fibers made of a thermoplastic polymer other than the thermoplastic polyurethane elastomer, a method of coating the roll surface with a silicon resin having a low surface free energy or a material of fluororesin is usually used in order to prevent adhesion of fibers to a roll and the like. The coating is worn away with progressing of the production, and at the time that the surface of a base layer is exposed, the fibers have a possibility of adhesion of the fibers to a roll and the like. The method is not preferred because of having an industrial problem.

PRIOR ARTS

Patent Document

Patent document 1: WO-H7-503502
Patent document 2: JP-A-2004-244791
Patent document 3: JP-A-2004-197291
Patent document 4: JP-A-2004-244793

SUMMARY OF THE INVENTION

Subject to be Solved by the Invention

It is an object of the present invention to provide a spunbonded non-woven fabric having excellent productivity such that fibers are not adhered on a roll and the like just after fiber deposition, and having excellent stretchability, touch and fuzz resistance.

Means for Solving the Subject

The present invention provides a spunbonded non-woven fabric which comprises long fibers made of a thermoplastic polyurethane elastomer (A) containing ethylene bis-oleic acid amide and/or crosslinked organic fine particles, having a hardness of 75 to 85 and obtainable by using 1,4-bis(2-hydroxyethoxy)benzene as a chain extender, and further provides a spunbonded non-woven fabric which comprises log fibers made of the thermoplastic polyurethane elastomer (A) and long fibers made of a thermoplastic resin (B) other than the thermoplastic polyurethane elastomer (A) and provides uses thereof.

Effect of the Invention

Since the spunbonded non-woven fabric of the present invention comprises long fibers made of a thermoplastic polyurethane elastomer having a relatively low hardness and has high stretching physical properties, good touch, fuzz resistance, it is suitable for sanitary materials made of the spunbonded non-woven fabric such as paper diapers and the like.

Since the long fibers made of the thermoplastic polyurethane elastomer having a relatively low hardness contained in the spunbonded non-woven fabric of the present invention contain ethylene bis-oleic acid amide and/or crosslinked organic fine particles, the spunbonded non-woven fabric can be produced stably with no adhesion thereof to a roll and the like just after fiber deposition during the production.

BRIEF DESCRIPTION OF DRAWING

FIG. 1 is a schematic view of a gear stretching device.

EMBODIMENT FOR CARRYING OUT THE INVENTION

Thermoplastic Polyurethane Elastomer (A)

The thermoplastic polyurethane elastomer (A) of the present invention (hereinafter, abbreviated to "TPU(A)") is a thermoplastic polyurethane elastomer (hereinafter, abbreviated to "TPU(a)") having a hardness (measured in JIS K-7311 by an A type durometer) of 75 to 85, preferably 80 to 85, more preferably 80 to 83 and containing ethylene bis-oleic acid amide and/or crosslinked organic fine particles. The thermoplastic polyurethane elastomer is known generically may be abbreviated as "TPU".

Even when TPU having a hardness of less than 75 is mixed with ethylene bis-oleic acid amide and/or crosslinked organic fine particles and mixed with long fibers made of a thermoplastic resin (B) other than TPU (hereinafter referred to "thermoplastic resin (B)"), a resulting spunbonded non-woven fabric has a possibility that the fabric is adhered on a roll and the like just after fiber deposition. On the other hand, when TPU having a hardness of over 85 is mixed with long fibers made of the thermoplastic resin (B) and molded by spun bonding, a resulting spunbonded non-woven fabric has a problem that the stretchability is poor.

In the thermoplastic polyurethane elastomer (A) of the present invention, it is preferred to use a thermoplastic polyurethane elastomer (A2) which comprises the thermoplastic polyurethane elastomer [TPU (a)] which is a thermoplastic polyurethane elastomer [TPU (a2)] obtainable by using 1,4-bis(2-hydroxyethoxy)benzene as a chain extender and further comprises ethylene bis-oleic acid amide and/or crosslinked organic fine particles, because when it is used as a material of a spunbonded non-woven fabric, and mixed with long fibers of the thermoplastic resin (B) to prepare a spunbonded non-woven fabric, the resulting spunbonded non-woven fabric has excellent stretchability.

The raw material of TPU(A) according to the present invention, namely the thermoplastic polyurethane elastomer [TPU(a)] prepared before adding ethylene bis-oleic acid amide and/or crosslinked organic fine particles has a fluid initiation temperature of preferably not lower than 155° C., more preferably 155 to 170° C. The thermoplastic polyurethane elastomer [TPU(a2)] obtainable by using 1,4-bis(2-hydroxyethoxy)benzene as a chain extender used for the thermoplastic polyurethane elastomer [TPU(a)] has a fluid initiation temperature of preferably not lower than 160° C., more preferably 160 to 175° C. Using TPU having a fluid initiation temperature in the above range, a spunbonded non-woven fabric having excellent productivity, stretchability, touch and fuzz resistance can be produced.

The expression "TPU(a)" may include the thermoplastic polyurethane elastomer TPU(a2) obtainable by using 1,4-bis(2-hydroxyethoxy)benzene as a chain extender unless otherwise provided notification.

TPU(a) of the present invention has a weight average molecular weight (Mw) of preferably from 125000 to 200000, more preferably 130000 to 180000, and a melt viscosity of from $0.9 \times 10^4$ to $1.4 \times 10^4$ (dPa·s). The thermoplastic polyurethane elastomer [TPU(a2)] obtainable by using 1,4-bis(2-hydroxyethoxy)benzene as a chain extender used for TPU(a) has a weight average molecular weight (Mw) of preferably from 95000 to 200000, more preferably 95000 to 170000, and a melt viscosity of from $0.4 \times 10^4$ to $1.3 \times 10^4$ (dPa·s). Using TPU having Mw and a melt viscosity in the above ranges as TPU(a), a spunbonded non-woven fabric can be produced stably.

TPU(a) of the present invention is preferred because the amount of massive matters such as fish eyes or gel generated during the production of TPU is small. These massive matters can be measured by a known method, for example, the method as described in JP-A-2004-244791. These massive matters are components caused by the raw materials for TPU and by the chemical reaction of the raw materials, such as a component derived from a hard segment condensate of TPU and a component obtainable by crosslinking a hard segment and/or a soft segment with allophanate bonding or burret bonding. When the amount of the massive matters is large, thread breakage and the like are caused and thereby the spunbonded non-woven fabric cannot be produced stably.

Polyol

A Polyol which is one component for constituting TPU(a) according to the present invention is a polymer having at least two hydroxyl groups in one molecule and examples thereof are polyoxyalkylene polyol, polytetramethylene ether glycol, polyester polyol, polycaprolactone polyol and polycarbonate diol. These polyols may be used singly or two or more may be mixed for use. Among these polyols, polyoxyalkylene polyol, polytetramethylene ether glycol and polyester polyol are preferred.

It is preferred that these polyols be sufficiently dehydration treated with heating under reduced pressure to decrease the moisture thereof. These polyols have a moisture content of preferably not more than 0.05% by weight, more preferably not more than 0.03% by weight, furthermore preferably not more than 0.02% by weight.

Polyoxyalkylene Polyol

Examples of polyoxyalkylene polyol are polyoxyalkylene glycols obtainable by addition polymerizing one or two or more bivalent alcohols having a relatively low molecular weight on an alkylene oxide such as propylene oxide, ethylene oxide, butylenes oxide and styrene oxide. In the addition polymerization, preferable examples of a polymerization catalyst are an alkali metal compound such as cesium hydroxide and rubidium hydroxide, and a compound having a P=N bond.

Among the alkylene oxides, propylene oxide and ethylene oxide are particularly preferred. When two or more alkylene oxides are used, the amount of propylene oxide is preferably not less than 40% by weight, more preferably not less than 50% by weight based on the total amount of alkylene oxides. Using an alkylene oxide containing propylene oxide in the above amount, polyoxy alkylene polyol can have an oxy propylene group content of not less than 40% by weight.

In order to improve durability and mechanical properties, TPU(a) of the present invention has a rate of primary hydroxylation at a molecule end of polyoxyalkylene polyol of preferably not less than 50% by mol, more preferably not less than 60% by mol. In order to improve the rate of primary hydroxylation, ethylene oxide is preferably copolymerized at a molecule end.

Polyoxyalkylene polyol has a number average molecular weight of preferably from 200 to 8000, more preferably 500 to 5000. In order to improve lowering of the glass transition point and fluidity of TPU(a), TPU(a) is preferably produced by mixing two or more polyoxyalkylene polyols having a different molecular weight and a different content of oxyalkylene group. Furthermore, the polyoxyalkylene polyol preferably contains a smaller amount of a mono-ol having an unsaturated group at a molecule end generated by a side reaction of the propylene oxide addition polymerization. The mono-ol content in polyoxyalkylene polyol is represented by a degree of total unsaturation as determined in JIS K-1557. The degree of total unsaturation of polyoxyalkylene polyol is preferably not more than 0.03 meq/g, more preferably not more than 0.02 meq/g. When the degree of total unsaturation is more than 0.03 meq/g, the heat resistance and durability of TPU are lowered. The lower limit of the degree of total unsaturation is preferably about 0.001 meq/g from the viewpoint of industrial production of polyoxyalkylene polyol.

Polytetramethylene Etherglycol

For TPU(a) of the present invention, it is possible to use, as a polyol, polytetramethylene ether glycol (hereinafter abbreviated to "PTMEG") obtainable by ring-opening polymerization of tetrahydrofurane. PTMEG has a number average molecular weight of preferably about 250 to 4000, more preferably about 250 to 3000.

Polyesterpolyol

Examples of polyesterpolyol are polyesterpolyols obtainable by condensation polymerization of one or two or more polyols having a low molecular weight with one or two or more carboxylic acid such as dicarboxylic acid having a low molecular weight and oligomeric acid.

Examples of polyols having a low molecular weight are ethylene glycol, diethylene glycol, propylene glycol, dipropylene glycol, 1,3-propane diol, 1,4-butane diol, 1,5-pentane diol, 1,6-hexane diol, glycerin, trimethyol propane, 3-methyl-1,5-pentane diol, hydrogenated bisphenol A and hydrogenated bisphenol F. Examples of dicarboxylic acid having a low molecular weight are glutaric acid, adipic acid, sebacic acid, terephthalic acid, isophthalic acid and dimer acid. Specific examples thereof are polyethylene butylenes adipate polyol, polyethylene adipate polyol, polyethylene propylene adipate polyol and polypropylene adipate polyol.

Polyester polyol has a number average molecular weight of preferably about 500 to 4000, more preferably about 800 to 3000.

Polycaprolactone Polyol

Polycaprolactone polyol is obtainable by ring-opening polymerization of ε-caprolactone.

Polycarbonate Diol

Examples of polycarbonate diol are polycarbonate diols obtainable by condensation reaction of a bivalent alcohol such as 1,4-butanediol and 1,6-hexanediol with a carbonate compound such as dimethyl carbonate, diethyl carbonate and diphenyl carbonate. Polycarbonate diol has a number average molecular weight of preferably about 500 to 3000, more preferably about 800 to 2000.

Isocyanate Compound

Examples of the isocyanate compound which is one component constituting TPU(a) according to the present invention are compounds of aromatic group, aliphatic group and alicyclic group which compounds have two or more isocyanate groups in one molecule.

Aromatic Polyisocyanate

Examples of aromatic polyisocyanates are 2,4-tolylene diisocyanate, 2,6-tolylene diisocyanate, a tolylene diisocyanate isomeric mixture containing 2,4-type and 2,6-type in a weight ratio of 80 to 20 (TDI-80/20), a tolylene diisocyanate isomeric mixture containing 2,4-type and 2,6-type in a weight ratio of 65 to 35 (TDI-65/35), 4,4'-diphenylmethane diisocyanate, 2,4'-diphenylmethane diisocyanate, 2,2'-diphenylmethane diisocyanate, and their diphenylmethane diisocyanate isomeric mixtures, tolylene diisocyanate, xylylene diisocyanate, tetramethylxylylene diisocyanate, paraphenylene diisocyanate, naphthalene diisocyanate.

Aliphatic Polyisocyanate

Examples of aliphatic polyisocyanates are ethylene diisocyanate, trimethylene diisocyanate, tetramethylene diisocyanate, hexamethylene diisocyanate, octamethylene diisocyanate, nonamethylene diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecamethylene triisocyanate, 1,3,6-hexamethylene triisocyanate, 1,8-diisocyanate-4-isocyanate methyloctane, 2,5,7-trimethyl-1,8-diisocyanate-5-isocyanate methyloctane, bis(isocyanate ethyl)carbonate, bis(isocyanate ethyl) ether, 1,4-butyleneglycohol dipropylether-ω,ω'-diisocyanate, lysine isocyanate methyl ester, lysine triisocyanate, 2-isocyanate ethyl-2,6-diisocyanate hexanoate, 2-isocyanate propyl-2,6-diisocyanate hexanoate and bis(4-isocyanate-n-butylidene)pentaerythritol.

Alicyclic Polyisocyanate

Examples of alicyclic polyisocyanates are isophorone diisocyanate, bis(isocyanate methyl)cyclohexane, dicyclohexylmethane diisocyanate, cyclohexane diisocyanate, methylcyclohexane diisocyanate, 2,2'-dimethyldicyclohexylmethane diisocyanate, dimmer acid diisocyanate, 2,5-diisocyanate methyl-bicyclo[2,2,1]-heptane, 2,6-diisocyanate methyl-bicyclo[2,2,1]-heptane, 2-isocyanatemethyl-2-(3-isocyanatepropyl)-5-isocyanate methyl-bicyclo[2,2,1]-heptane, 2-isocyanatemethyl-2-(3-isocyanatepropyl)-6-isocyanate methyl-bicyclo[2,2,1]-heptane, 2-isocyanatemethyl-3-(3-isocyanatepropyl)-5-(2-isocyanate ethyl)-bicyclo[2,2,1]-heptane, 2-isocyanatemethyl-3-(3-isocyanatepropyl)-6-(2-isocyanate ethyl)-bicyclo[2.2.1]-heptane, 2-isocyanatemethyl-2-(3-isocyanatepropyl)-5-(2-isocyanate ethyl)-bicyclo[2.2.1]-heptane and 2-isocyanate methyl-2-(3-isocyanatepropyl)-6-(2-isocyanate ethyl)-bicyclo[2,2,1]-heptane.

Furthermore, examples of polyisocyanates are modified polyisocyanates such as urethane modified polyisocyanate, carbodiimide modified polyisocyanate, urethoimine modified polyisocyanate, biuret modified polyisocyanate, allophanate modified polyisocyanate and isocyanurate modified polyisocyanate.

Of these polyisocyanates, it is preferred to use 4,4'-diphenylmethane diisocyanate (hereinafter abbreviated to "MDI"), hydrogenated MDI (dicyclohexylmethane diisocyanate, hereinafter abbreviated to "HMDI"), paraphenylene diisocyanate (hereinafter abbreviated to "PPDI"), naphthalene diisocyanate (hereinafter abbreviated to "NDI"), hexamethylene diisocyanate (hereinafter abbreviated to "HDI"), isophorone diisocyanate (hereinafter abbreviated to "IPDI"), 2,5-diisocyanatemethyl-bicyclo[2,2,1]-heptane (hereinafter abbreviated to "2,5-NBDI"), 2,6-diisocyanate methyl-bicyclo[2,2,1]-heptane (hereinafter abbreviated to "2,6-NBDI"). It is more preferred to use MDI, HDI, HMDI, PPDI, 2,5-NBDI and 2,6-NBDI. Moreover, it is also preferred to use modified diisocyanates of above preferred diisocyanates, such as urethane modified diisocyanate, carbodiimide modified diisocyanate, urethoimine modified diisocyanate and isocyanurate modified diisocyanate.

Chain Extender

Examples of the chain extender used for the production of TPU(a) are preferably aliphatic, aromatic, complex cyclic or alicyclic polyols having at least two hydroxyl groups in one molecule and a low molecular weight. The chain extender preferably has a decreased content of moisture by sufficiently carrying out dehydration treatment with heating under reduced pressure. The chain extender has a moisture content of preferably not more than 0.05% by weight, more preferably not more than 0.03% by weight, furthermore preferably not more than 0.02% by weight.

Examples of aliphatic polyols are ethylene glycol, propylene glycol, 1,3-propane diol, 1,4-butane diol, 1,5-pentane diol, 1,6-hexane diol, glycerin and trimethylol propane. Examples of aromatic, complex cyclic and alicyclic polyols are paraxylene glycol, bis(2-hydroxyethyl) terephthalate, bis (2-hydroxyethyl)isophthalate, 1,4-bis(2-hydroxyethoxy) benzene, 1,3-bis(2-hydroxyethoxy)benzene, resorcin, hydroquinone, 2,2'-bis(4-hydroxycyclohexyl)propane, 3,9-bis(1, 1-dimethyl-2-hydroxyethyl)-2,4,8,10-tetraoxaspiro[5,5] undecane, 1,4-cyclohexane dimethanol and 1,4-cyclohexane diol.

These chain extenders may be used singly or two or more may be mixed for use.

Among these chain extenders, 1,4-bis(2-hydroxyethoxy) benzene is preferably used because the spunbonded non-woven fabric having more excellent stretchability can be produced stably without adhesion of the fabric to a roll and the like.

Ethylene Bisoleic Acid Amide

Ethylene bisoleic acid amide which is one component for adding to TPU(a) according to the present invention is a compound obtainable from ethylene diamine and oleic acid.

To TPU(a), ethylene bisoleic acid amide according to the present invention is added in an amount of usually 0.3 to 2.0% by mass, preferably 0.4 to 0.8% by mass. Adding to ethylene bisoleic acid amide in the above amount, TPU(a) can be extruded stably and adhesion of the fabric to a roll and the like can be prevented stably in the production of the spunbonded non-woven fabric.

Crosslinked Organic Fine Particles

The crosslinked organic fine particles which are one component for adding to TPU (a) according to the present invention are fine particles which are not molten in melt spinning TPU(a), have an average particle diameter of usually 0.5 to 8 μm, preferably 1 to 4 μm and comprise a crosslinked polymer.

Examples of the crosslinked organic fine particles comprise a crosslinked polymer obtainable by polymerizing one or two or more of the following compounds with the following crosslinking agent. Examples of the compounds are:

(meth)acrylates such as (meth)acrylic acid, methyl(meth) acrylate, ethyl(meth)acrylate, n-propyl(meth)acrylate, isopropyl(meth)acrylate, n-butyl(meth)acrylate, iso-butyl (meth)acrylate, t-butyl(meth)acrylate, 2-ethylhexyl(meth) acrylate, cyclohexyl(meth)acrylate, benzyl(meth)acrylate, hydroxyethyl(meth)acrylate and hydroxypropyl(meth)acrylate;

styrenes such as styrene, p-methylstyrene, vinyltoluene and p-t-butylstyrene;

maleimides such as N-phenyl maleimide, N-cyclohexyl maleimide and N-benzyl maleimide;

(meth)acrylamides such as (meth)acrylamide and N-methylol (meth)acrylamide;

acrylo nitriles such as (meth)acrylo nitrile and the like; and N-vinyl pyrrolidone.

Examples of the crosslinking agent are polyfunctional (meth)acrylates such as, ethylene glycol di(meth)acrylate, diethylene glycol di(meth)acrylate, propylene glycol di(meth)acrylate, neopentylglycol di(meth)acrylate, trimethylol propane tri(meth)acrylate and bishydroxymethyl bisphenol A di(meth)acrylate;

radical polymerizable crosslinking agents such as divinyloxy ethoxy (meth)acrylate, diallylphthalate, allyl(meth) acrylate and divinyl benzene;

polyfunctional epoxy compounds such as bisphenol A diglycidyl ether, diethylene glycol diglycidyl ether and neopentylglycol diglycidyl ether;

polyfunctional isocyanate compounds such as tolylene diisocyanate, xylylene diisocyanate and isophorone diisocyanate; N-methylol melamine and N-methylol benzoguanamine. The crosslinked organic fine particles preferably comprise a crosslinked acryl resin containing a (meth)acrylate as a main component because of having excellent heat resistance.

The crosslinked organic fine particles according to the present invention are added in an amount of usually 0.3 to 2.0% by mass, preferably 0.4 to 2.0% by mass, more preferably 0.8 to 1.0% by mass to TPU(a). When the crosslinked organic fine particles are added in the above amount, TPU(a) can be extruded stably and adhesion of the fabric to a roll and the like can be stably prevented in the production of the spunbonded non-woven fabric.

In the combined use of ethylene bisoleic acid amide and the crosslinked organic fine particles, the total amount thereof is from 0.3 to 2.0% by mass, preferably 0.4 to 2.0% by mass, more preferably 0.8 to 1.0% by mass or the above amount may apply each of ethylene bisoleic acid amide and the crosslinked organic fine particles.

Other Thermoplastic Elastomer

TPU(A) or TPU(a) according to the present invention may be mixed with various known thermoplastic elastomers such as a polystyrene elastomer, a polyolefin elastomer, a polyvinylchloride elastomer, a polyester elastomer, a polyamide elastomer and a thermoplastic polyurethane elastomer other than TPU(a) within not missing the object of the present invention.

Additive

To TPU(A) or TPU(a) according to the present invention, various known additives such as an antioxidant, a heat stabilizer, a weather stabilizer, an antistatic agent, a slipping agent, an antifogging agent, a lubricant, a dye, a pigment, a natural oil, a synthetic oil and a wax may be added within not missing the object of the present invention.

Examples of the additives are a hindered phenol antioxidant such as 2,6-di-t-butyl-4-methylphenol (BHT), pentaerythritol tetrakis[3-(3,5-di-t-butyl-4-hydroxyphenyl)propionate] (Trade name: Irganox1010 manufactured by Ciba Specialty Inc.), 6-(3,5-di-t-butyl-4-hydroxyphenyl)propionic acid alkyl ester and 2,2'-oxamide bis[ethyl-3-(3,5-di-t-butyl-4-hydroxyphenyl)]propionate; an aliphatic acid metal salt such as zinc stearate, calcium stearate and 1,2-hydroxystrearic acid calcium; and a polyvalent alcohol aliphatic acid ester such as glycerin monostearate, glycerin distearate, pentaerythritol monostearate, pentaerythritol distearate and pentaerythritol tristearate. These may be used singly or two or more may be combined for use.

Process for Producing Thermoplastic Polyurethane Elastomer (a)

The TPU(a) of the present invention is produced by selecting polyole, an isocyanate compound and a chain extender each having an optimum chemical structure as the raw materials of TPU(a). In the production, the hard segment amount is preferably 20 to 60% by weight, more preferably 22 to 50% by weight, most preferably 25 to 35% by weight wherein the hard segment amount is a weight percent value (% by weight) obtainable by dividing the total amount of the isocyanate compound and the chain extender used in the production of TPU by the total amount of polyol, the isocyanate compound and the chain extender, and multiplying 100.

Examples of the process for producing TPU(a) are (i) a process of allowing an end isocyanate group-having prepolymer prepared by allowing polyol to react with a isocyanate compound (hereinafter, referred to "prepolymer") to react with the chain extender (hereinafter, referred to "prepolymer process") and (ii) a process of mixing polyol with the chain extender and allowing the resulting mixture to react with an isocyanate compound (hereinafter, referred to "one shot process"). Of these production processes, it is preferred to prepare TPU by the prepolymer process from the viewpoint of mechanical properties and quality of the resulting TPU.

In the prepolymer process, the prepolymer is produced by mixing polyol and the isocyanate compound with stirring at a reaction temperature of about 40 to 250° C. for 30 sec to 8 hr in the presence of an inert gas. Next, the prepolymer and the chain extender are thoroughly mixed with stirring at a high rate in an amount such that the isocyanate index is preferably from 0.9 to 1.2, more preferably 0.95 to 1.15, furthermore preferably 0.97 to 1.08. The prepolymer and the chain extender are mixed and polymerized at a temperature of usually 80 to 300° C., preferably 80 to 260° C., most preferably 90 to 220° C. although the temperature is properly determined according to the melting point of the chain extender and the viscosity of the prepolymer. The polymerization time is preferably from 2 sec to 1 hr.

In the one shot process, polyol and the chain extender are mixed and defoamed, and the mixture and the isocyanate compound are mixed with stirring at a temperature of 40 to 280° C., more preferably 100 to 260° C. for 30 sec to 1 hr and thereby the polymerization reaction is progressed. In the one shot process, the isocyanate index is preferably in the same range as that in the prepolymer process.

Process for Producing Thermoplastic Polyurethane Elastomer (A)

TPU(A) of the present invention is prepared by adding the desired amounts of ethylene bisoleic acid amide and/or the crosslinked organic fine particles to TPU(a) prepared by the above production process. An example of the process of adding ethylene bisoleic acid amide and/or the crosslinked organic fine particles to TPU(a) is a process of pulverizing TPU(a), adding the desired amounts of ethylene bisoleic acid amide and/or the crosslinked organic fine particles and melt kneading them using an extruder.

Thermoplastic Resin (B)

For the thermoplastic resin (B) which is a raw material other than TPU(a) for forming long fibers of the spunbonded non-woven fabric of the present invention, various known thermoplastic resins other than TPU(a) can be used. The thermoplastic resin (B) is a resinous polymer different from TPU(a) and is usually a crystalline polymer having a melting point (Tm) of not lower than 100° C. or a non-crystalline polymer having a glass transition temperature of not lower than 100° C. The thermoplastic resin (B) is preferably the crystalline thermoplastic resin.

As the thermoplastic resin (B), a thermoplastic resin (extendable thermoplastic resin) having such properties that the non-woven fabric prepared by a known process for producing a spunbonded non-woven fabric has a maximum point elongation of not less than 50%, preferably not less than 70%, more preferably not less than 100%, and has little elastic recovery is preferred because when a spunbonded non-woven fabric prepared by mixing the thermoplastic resin and the long fibers of TPU(a) is stretched and processed, more bulkiness is expressed and the touch is better and further the elongation end function can be add to the spunbonded non-woven fabric. The upper limit of the maximum point elongation of the spunbonded non-woven fabric made of the thermoplastic resin (B), which is not particularly limited, is usually not more than 300%.

Examples of the thermoplastic resin (B) are a polyolefin which is a homopolymer or copolymer of α-olefins such as ethylene, propylene, 1-butene, 1-hexene, 4-methyl-1-pentene and 1-octene such as, high pressure low density polyethylene, linear low density polyethylene (LLDPE), high density polyethylene (HDPE), polypropylene (propylene homopolymer), a polyolefin (such as polypropylene random copolymer, poly-1-butene, poly-4-methyl-1-pentene, ethylene/propylene random copolymer, ethylene/1-butene random copolymer and propylene/1-butene random copolymer);

a polyester (such as polyethylene terephthalate, polybutylene terephthalate and polyethylene naphthalate), a polyamide (such as nylon-6, nylon-66 and polymethaxylene adipamide), polyvinylchloride, polyimide, ethylene/vinylacetate copolymer, ethylene/vinylacetate/vinylalcohol copolymer, ethylene/(meth)acrylic acid copolymer, ethylene-acrylate-carbon monoxide copolymer, polyacrylonitrile, polycarbonate, polystyrene, ionomer and their mixtures.

More preferable examples are high-pressure low-density polyethylene, linear low-density polyethylene (LLDPE), high density polyethylene, a propylene polymer such as polypropylene and a polypropylene random copolymer, polyethylene terephthalate and polyamide.

Of these thermoplastic resins (B), polyolefin is preferred and a propylene polymer is particularly preferred from the viewpoint of spinning stability at the time of molding and stretching processability of the non-woven fabric.

Preferable examples of the propylene polymer are a propylene homopolymer having a melting point (Tm) of not lower than 155° C., preferably 157 to 165° C. and a copolymer of propylene and a slight amount of at least one or two or more α-olefins having at least two carbon atoms (excluding 3 carbon atoms), preferably 2 to 8 carbon atoms (excluding 3 carbon atoms) such as ethylene, 1-butene, 1-pentene, 1-hexene, 1-octene and 4-methyl-1-pentene.

The melt flow rate (MFR: ASTM D-1238, 230° C., a load of 2160 g) of the propylene polymer is not particularly limited as long as melt spinning can be carried out. The melt flow rate of the propylene polymer is usually 1 to 1000 g/10 min, preferably 5 to 500 g/10 min, more preferably 10 to 100 g/10 min. The propylene polymer of the present invention has a ratio Mw/Mn of weight average molecular weight (Mw) to number average molecular weight (Mn) of usually 1.5 to 5.0. Furthermore, the ratio is preferably in the range of 1.5 to 3.0 because the spinning properties are good and fibers having more excellent fiber strength can be prepared. Mw and Mn can be measured using GPC (gel permeation chromatography) by a known method.

The olefin polymer composition prepared by adding HDPE in a small amount of 1 to 20% by weight, preferably 2 to 15% by weight, furthermore preferably 4 to 10% by weight based on 100% by weight of the total amount of the propylene polymer and HDPE to the propylene polymer is preferred from the viewpoint of spinning properties and stretching processability because it is possible to further improve the stretching processing properties of the resulting spunbonded non-woven fabric.

HDPE for adding to the propylene has a density, which is not particularly limited, of usually 0.94 to 0.97 g/cm$^3$, preferably 0.95 to 0.97 g/cm$^3$, more preferably 0.96 to 0.97 g/cm$^3$. Moreover, HDPE has a melt flow rate, which is not particularly limited as long as it has spinning properties, of usually 0.1 to 100 g/10 min, preferably 0.5 to 50 g/10 min, more preferably 1 to 30 g/10 min from the viewpoint of expressing elongation properties, wherein the melt flow rate MFR is determined by ASTM D-1238 at 190° C. under a load of 2160 g. The expression "good spinning properties" in the present invention means that fiber cut is not caused and fiber fusion is not caused at the time of outputting from a spinning nozzle and during stretching.

Additive

To the thermoplastic resin (B) of the present invention, various known additives such as an antioxidant, a heat stabilizer, a weather stabilizer, an antistatic agent, a slipping agent, an antifogging agent, a lubricant, a dye, a pigment, a natural oil, a synthetic oil and a wax can be added previously as an optional component within not missing the object of the present invention.

Examples of the additives are a hindered phenol antioxidant such as 2,6-di-t-butyl-4-methylphenol (BHT), pentaerythritol tetrakis[3-(3,5-di-t-butyl-4-hydroxyphenyl)propionate](Trade name: Irganox1010, manufactured by Ciba Specialty Inc.), 6-(3,5-di-t-butyl-4-hydroxyphenyl)propionic acid alkyl ester, 2,2'-oxamide bis[ethyl-3-(3,5-di-t-butyl-4-hydroxyphenyl)]propionate; an aliphatic acid metal salt such as zinc stearate, calcium stearate and 1,2-hydroxycalcium stearate; a polyvalent alcohol aliphatic acid ester such as glycerin monostearate, glycerin distearate, pentaerythritol monostearate, pentaerythritol distearate and pentaerythritol tristearate. These may be used singly or two or more may be combined for use.

Spunbonded Non-Woven Fabric

The spunbonded non-woven fabric of the present invention is a spunbonded non-woven fabric containing long fibers of TPU (A). It is not particularly limited as long as it contains the long fibers of TPU(A). It comprises only the long fibers of TPU(A) or furthermore comprises other fibers additionally.

The spunbonded non-woven fabric of the present invention preferably comprises the long fibers of TPU(A) and the long fibers of the thermoplastic resin (B), and more preferably comprises the long fibers of TPU(A) and the long fibers of the thermoplastic resin (B) in a proportion of 10/90% by mass to 90/10% by mass based on 100% by weight of the total weight of (A) and (B). When the spunbonded non-woven fabric contains other resins in addition to the long fibers of TPU(A), it has improved touch and flexibility and can be suitably used for sanitary materials such as paper diapers and the like.

The spunbonded non-woven fabric of the present invention more preferably comprises the long fibers of TPU(A) in an amount of preferably not less than 20% by mass, more preferably not less than 30% by mass from the viewpoints of stretchability and flexibility, and it furthermore comprise the long fibers of TPU(A) in an amount of preferably not more than 70% by mass, more preferably not more than 60% by mass from the viewpoint of processing properties (resistance to tackiness).

The spunbonded non-woven fabric of the present invention has excellent stretching properties (hereinafter sometimes referred to "stretching properties (I)") as compared with those of conventional spunbonded non-woven fabrics because of containing the long fibers of TPU (A). The stretching properties are represented by a stress ratio ($S_1/S_2$) in the following way. For example, a specimen having a size of 200 mm(MD)× 25 mm (CD) is prepared from the spunbonded non-woven fabric. Using a universal tensile testing machine (IM-201 type, manufactured by Intesco Co., Ltd.), the specimen is stretched by 100% in a sample width of 25 mm, in a chuck distance of 100 mm at a tensile rate of 300 mm/min and thereafter, the specimen is recovered until the original size at the same rate. This cycle is repeated twice. The value after the two cycle repetition (stress at the time of 50% stretching ($S_1$)÷stress at the time of 50% recovery ($S_2$)), namely, stress ratio ($S_1/S_2$) is taken as the stretching properties.

As the stretching properties (I) are smaller, they are more excellent. Furthermore, the stretching properties depend on the amount of the long fibers of TPU(A) contained in the spunbonded non-woven fabric. For example, when the amount of the long fibers of TPU(A) is 70% by mass and the stretching properties are not more than 1.72, when it is 55% by mass and the stretching properties are not more than 1.82, when it is 50% by mass and the stretching properties are not more than 1.87, when it is 40% by mass and the stretching properties are not more than 1.94, or when it is 30% by mass and the stretching properties are not more than 2.01, the resulting spunbonded non-woven fabric has excellent stretching properties even after stretching. Furthermore, 1,4-bis(2-hydroxyethoxy)benzene is preferably used as the chain extender because the resulting spunbonded non-woven fabric has more excellent stretching properties.

The long fibers of TPU(A) and the long fibers of the thermoplastic resin (B) for forming the spunbonded non-woven fabric according to the present invention each have an average fiber diameter of usually not more than 50 µm, preferably not more than 40 µm, more preferably not more than 30 µm. The fiber diameter of the long fibers of TPU(A) may be the same as or different from that of the long fibers of the thermoplastic resin (B).

The spunbonded non-woven fabric of the present invention has a basis weight in terms of the total laminate of usually not more than 120 g/m$^2$, preferably not more than 80 g/m$^2$, more preferably not more than 50 g/m$^2$, furthermore preferably 40 to 15 g/m$^2$ from the viewpoints of flexibility and permeability in the sanitary material use such as diapers and the like.

The spunbonded non-woven fabric of the present invention may be a single layer or a laminate of two or more layers. When the spunbonded non-woven fabric is the laminate of two or more layers, one laminate has such a proportion (fiber combining ratio) of the long fibers of TPU(A) and the long fibers of the thermoplastic resin (B) in the spunbonded non-woven fabric of each layer such that it may be same as or different from that of the other layer.

When spunbonded non-woven fabrics having a different fiber combining ratio are laminated, the laminate may comprise a spunbonded non-woven fabric containing only the long fibers of TPU(A), a spunbonded non-woven fabric containing over 90% by mass of the long fibers of TPU(A), a spunbonded non-woven fabric containing only the long fibers of the thermoplastic resin (B) or a spunbonded non-woven fabric containing over 90% by mass of the long fibers of the thermoplastic resin (B). When the laminate comprises a layer of a spunbonded non-woven fabric having a proportion of the long fibers of TPU(A) or a proportion of the long fibers of the thermoplastic resin (B) beyond the above range, the proportion of the long fibers of TPU(A) in the whole laminate is preferably in the above range.

The fiber-combining ratio indicates a proportion of specific kinds of fibers in a layer of a spunbonded non-woven fabric obtainable by mixing two or more kinds of fibers or a mixing proportion of each kind of fibers in the non-woven fabric layer. That is to say, in the layer of a spunbonded non-woven fabric which comprises TPU(A) and the thermoplastic resin (B), the fiber-combining ratio of the long fibers of TPU(A) is determined by dividing the weight of the long fibers of TPU (A) with the total weight of the long fibers of TPU(A) and the long fibers of the thermoplastic resin (B) [the weight of the long fibers of TPU(A)/(the weight of the long fibers of TPU (A)+the weight of the long fibers of the thermoplastic resin (B))]. The fiber-combining ratio of the long fibers of the thermoplastic resin (B) is determined by dividing the weight of the long fibers of the thermoplastic resin (B) with the total weight of the long fibers of TPU (A) and the long fibers of the thermoplastic resin (B) [the weight of the long fibers of thermoplastic resin (B)/(the weight of the long fibers of TPU(A)+ the weight of the long fibers of the thermoplastic resin (B))]. Furthermore, in the layers of the spunbonded non-woven fabrics formed from TPU(A) and the thermoplastic resin (B), the expression that the fiber combining ratio is different means that the fiber combining ratio of (A) and (B) is different in each of the non-woven fabric layers.

In the spunbonded non-woven fabric laminate having at least two layers, at least one layer is preferably a spunbonded non-woven fabric layer (C-1) which comprises the long fibers of TPU(A) in an amount of preferably 40 to 95% by weight, more preferably 40 to 90% by weight, furthermore preferably 50 to 80% by weight and the long fibers of the thermoplastic resin (B) in an amount of preferably 60 to 5% by weight, more preferably 60 to 10% by weight, furthermore preferably 50 to 20% by weight provided that the total of (A) and (B) is 100% by weight. The other layer is preferably a spunbonded non-woven fabric layer (C-2) which comprises the long fibers of TPU(A) in an amount of preferably 10 to 60% by weight, more preferably 10 to 55% by weight, furthermore preferably 10 to 50% by weight and the long fibers of the thermoplastic resin (B) in an amount of preferably 90 to 40% by weight, more preferably 90 to 45% by weight, furthermore preferably 90 to 50% by weight provided that the total of (A) and (B) is 100% by weight.

The spunbonded non-woven fabric layers (C-1) and (C-2) may be laminated continuously or may be laminated through another spunbonded non-woven fabric layer, a melt blown non-woven fabric layer, a film layer or an adhesive layer.

As another embodiment of the present invention, there is a non-woven fabric laminate having three layers of fiber combined spunbonded non-woven fabrics such that the laminate has at least three layers containing the long fibers of TPU (A) and the long fibers of the thermoplastic resin (B), and the fiber mixed spunbonded non-woven fabric layer placed in the middle of the three spunbonded non-woven fabric layers (intermediate layer) has a fiber combining ratio of the thermoplastic elastomer (A) larger than that of each of the other two layers.

In the other spunbonded non-woven fabric layers placed on both sides of the intermediate layer, the fiber combining ratio of the long fibers of the thermoplastic elastomer (A) may be the same as or different from each other. It is unnecessary that the three fiber combined spunbonded layers are laminated continuously. The three fiber combined spunbonded layers may be laminated through another spunbonded non-woven fabric layer, a melt blown non-woven fabric, a film layer or an adhesive layer. Moreover, on at least one outside or both outsides of the three layered laminate, another fiber combined non-woven fabric layer may be laminated and the fiber combined non-woven fabric layer has a fiber combining ratio of TPU(A) larger than or smaller than that of the intermediate layer.

Specifically, the intermediate layer is preferably a spunbonded non-woven fabric layer (D-1) which comprises the long fibers of TPU(A) in an amount of preferably 40 to 100% by weight, more preferably 40 to 95% by weight, furthermore preferably 50 to 90% by weight and the long fibers of the thermoplastic resin (B) in an amount of preferably 60 to 0% by weight, more preferably 60 to 5% by weight, furthermore preferably 50 to 10% by weight provided that the total of (A) and (B) is 100% by weight.

The two spunbonded non-woven fabric layers which are placed on both sides of the intermediate layer are a spunbonded non-woven fabric layer (D-2) which comprises the long fibers of TPU(A) in an amount of preferably 10 to 60% by weight, more preferably 10 to 55% by weight, furthermore preferably 10 to 50% by weight and the long fibers of the thermoplastic resin (B) in an amount of preferably 90 to 40% by weight, more preferably 90 to 45% by weight, furthermore preferably 90 to 50% by weight, and a spunbonded non-woven fabric layer (D-3) which comprises the long fibers of TPU(A) in an amount of preferably 10 to 60% by weight, more preferably 10 to 55% by weight, furthermore preferably 10 to 50% by weight and the long fibers of the thermoplastic resin (B) in an amount of preferably 90 to 40% by weight, more preferably 90 to 45% by weight, furthermore preferably 90 to 50% by weight provided that the total of (A) and (B) is 100% by weight.

In the spunbonded non-woven fabric laminate, the intermediate layer (D-1) has a fiber combining rate of the long fibers of TPU(A) larger than those of the spunbonded non-woven fabric layers (D-2) and (D-3).

The fiber combining ratios of the long fibers of TPU (A) in the two spunbonded non-woven fabric layers (D-2) and (D-3) which are placed on both sides of the intermediate layer (D-1) may be same as or different each other. It is preferred that the difference between the fiber combining ratios of the long fibers of TPU(A) in the two spunbonded non-woven fabric layers (D-2) and (D-3) be preferably not more than 40%, more preferably not more than 30%, furthermore preferably not more than 20%, specially preferably 10 to 0% and the difference between the basis weights of (D-2) and (D-3), namely the values of (D-1)/(D-2) and (D-1)/(D-3) be preferably 2 to 0.5, more preferably 1.5 to 0.67, furthermore preferably 1.2 to 0.83, specially preferably 1.1 to 0.91 because the productivity can be enhanced.

Process for Producing Spunbonded Non-Woven Fabric

The spunbonded non-woven fabric of the present invention can be produced using TPU(A) or TPU(A) and the thermoplastic resin (B) by a known production process of spunbonded non-woven fabrics, for example, the process as described in JP-A-2004-244791.

Specifically, the spunbonded non-woven fabric can be produced by the following process of:

(I) a step of melting the thermoplastic polyurethane elastomer (A) containing ethylene bisoleic acid amide and/or crosslinked organic fine particles and having a hardness of 75 to 85, or TPU(A) and the thermoplastic resin (B) other than the thermoplastic polyurethane elastomer (A) respectively, (II) a step of extruding the thermoplastic polyurethane elastomer (A), or TPU(A) and the thermoplastic resin (B) respectively from different nozzles provided on the same die simultaneously and depositing mixed fibers of long fibers of the thermoplastic polyurethane elastomer (A), or long fibers of TPU(A) and long fibers of the thermoplastic resin (B) by spinning, and (III) a step of partly fusing the deposit prepared in the above.

More specifically, TPU(A) or TPU(A) and the thermoplastic resin (B) are melted by different extruders respectively, and the molten polymers are introduced respectively into dies equipped with a large number of spinning nozzles. TPU(A) and the thermoplastic resin (B) are output simultaneously from different spinning holes respectively. Thereafter, the long fibers of TPU(A) and the long fibers of the thermoplastic resin (B) molten and spun are introduced into a cooling room and cooled with cool air. The long fibers are stretched by stretching air and are deposited on a movable collecting surface. The melting temperature of the polymers is not particularly limited as long as it is higher than the softening temperature or melting temperature of each polymer and lower than the thermolysis temperature, and it can be determined by the polymer for use. The die temperature depends on the polymer for use. For example, when a propylene polymer or an olefin polymer composition of a propylene polymer and HDPE is used as the thermoplastic resin (B), the die temperature is determined in the range of usually 180 to 240° C., preferably 190 to 230° C., more preferably 200 to 225° C.

The temperature of the cooling air is not particularly limited as long as the polymer can be solidified. For example, the temperature of the cooling air is in the range of usually 5 to 50° C., preferably 10 to 40° C., more preferably 15 to 30° C. The air rate of the stretching air is in the range of usually 100 to 10,000 m/min, preferably 500 to 10,000 m/min.

The mixed fibers are deposited in a web form on the movable collecting surface by the above method, and then the deposit is transported by contacting with a rotational device such as a belt, a nip roll and the like. Thereafter, the deposit is subjected to confounding treatment by needle punch, water jet or ultrasonic sealing, or heat fusion treatment by heat embossing roll and thereby the deposit is fused partly. It is preferred to employ heat fusion treatment by heat embossing roll. The embossing temperature is usually from 50 to 160° C., preferably 60 to 150° C. The embossed area ratio by embossing roll can be determined appropriately. The embossed area ratio is preferably 5 to 30%.

Stretchable Spunbonded Non-Woven Fabric

The stretchable spunbonded non-woven fabric of the present invention is a non-woven fabric obtainable by stretching the above spunbonded non-woven fabric. Since the spunbonded non-woven fabric comprises the long fibers of TPU (A) and other fibers, the non-woven fabric obtainable by stretching has excellent touch, flexibility and stretchability and can be favorably used for sanitary materials such as paper diapers and the like.

A specimen is prepared from the stretchable spunbonded non-woven fabric. Using a universal tensile testing machine (IM-201 type, manufactured by Intesco Co., Ltd.), the specimen is stretched by 100% in a sample width of 25 mm, in a chuck distance of 100 mm at a tensile rate of 300 mm/min and thereafter, the specimen is recovered until the original size at the same rate. This cycle is carried out. The value after the cycle (stress at the time of 50% stretching ($S_1$)÷stress at the time of 50% recovery ($S_2$)), namely, stress ratio ($S_1/S_2$) is taken as the stretching properties (hereinafter sometime referred to "stretching properties (II)"). The stretchable spunbonded non-woven fabric of the present invention has a more excellent stress ratio ($S_1/S_2$) than that of the spunbonded non-woven fabric containing the long fibers of TPU(A) before stretching.

Similar to the stretching properties (I), the stretching properties (II) depends on the amount of the long fibers of TPU (A). For example, when the amount of the long fibers of TPU(A) is 70% by mass and the stretching properties are not more than 1.61, when it is 55% by mass and the stretching properties are not more than 1.71, when it is 50% by mass and the stretching properties are not more than 1.75, when it is 40% by mass and the stretching properties are not more than 1.88, or when it is 30% by mass and the stretching properties are not more than 1.89, the resulting spunbonded non-woven fabric has excellent stretching properties. TPU(A2) is preferably used as TPU(A) because the resulting stretchable spunbonded non-woven fabric has more excellent stretching properties.

Process for Producing Stretchable Spunbonded Non-Woven Fabric

The stretchable spunbonded non-woven fabric of the present invention can be obtained by stretching processing the above spunbonded non-woven fabric. As the process for stretching processing, conventionally known processes are applicable. It may be a partly stretching process or an overall stretching process. Moreover, it may be mono-axial stretching or bi-axial stretching. As the process for stretching in a machine flow direction (MD), for example, the partly fused mixed fibers are passed through two or more nip rolls. During passing the fibers, the partly fused mixed fibers can be stretched by increasing the rotation rates of the nip rolls in order of the MD direction. FIG. 1 shows a gear stretching device equipped with a pair of gear rolls. Using the gear stretching device as shown in FIG. 1, the spunbonded non-woven fabric 2 can be processed with gear stretching.

The stretching magnification is preferably not less than 50%, more preferably not less than 100%, furthermore preferably not less than 200%, and preferably not more than 1000%, more preferably not more than 400%. In the case of mono-axial stretching, the preferred stretching magnification is carried out in any of the MD direction and the CD direction vertical to the MD direction. In the case of two-axial stretching, the preferred stretching magnification is carried out in both of the MD direction and the CD direction vertical to the MD direction. Carrying out the stretching processing in such a stretching magnification, the stretchable non-woven fabric has a fiber diameter of usually not more than 50 µm, preferably not more than 40 µm, more preferably not more than 30 µm.

The stretchable non-woven fabric thus prepared has excellent fuzz resistance, touch and stretchability which are suitable for sanitary materials such as disposable diapers, sanitary napkins, bladder control pads and the like. Particularly, the stretchable non-woven fabric having more excellent effects can be prepared by stretching and processing the mixed fibers containing the long fibers of TPU(A) and the long fibers of the polymers of polyethylene and/or polypropylene and having expansion properties in the above stretching magnification.

The spunbonded non-woven fabric of the present invention may be laminated on one side or both sides thereof with other layers. The other layers laminated on the spunbonded non-woven fabric are particularly not limited and various kinds of layers can be laminated thereon according to the use.

Examples of the other layers are knitting fabrics, woven fabrics, non-woven fabrics and films. When the other layers are laminated (adhered) to the non-woven fabric laminate of the present invention, it is possible to employ various known methods, for example, a heat fusion method such as heat embossing processing and ultrasonic fusion, a mechanical confounding method such as needle punch and water jet, a method of using an adhesive agent such as a hot melt adhesive agent and a urethane adhesive agent, and extrusion laminating.

Examples of the non-woven fabric laminated on the spunbonded non-woven fabric of the present invention may include various known non-woven fabrics such as a spunbonded non-woven fabric other than the spunbonded non-woven fabric of the present invention, a melt blown non-woven fabric, a wet non-woven fabric, a dry non-woven fabric, a dry pulp non-woven fabric, a flash spinning non-woven fabric and split non-woven fabric. These non-woven fabrics may be non-stretchable non-woven fabrics. The non-stretchable non-woven fabrics have a MD or CD elongation at rupture of about 50% and do not cause return stress after stretching.

The film laminated on the spunbonded non-woven fabric of the present invention is preferably a film having permeability (moisture permeability) which can make the best use of the permeability of the spunbonded non-woven fabric of the present invention. As the film having permeability, various known films having permeability are used. Specific examples thereof are films made of a thermoplastic elastomer having moisture permeability such as polyurethane elastomer, polyester elastomer and polyamide elastomer, and porous films obtainable by stretching films made of a thermoplastic resin containing inorganic or organic fine particles. Examples of the thermoplastic resin preferably used for the porous films are polyolefins such as high pressure low density polyethylene, linear low density polyethylene (namely, LLDPE), high density polyethylene, polypropylene, polypropylene random copolymer and compositions thereof.

The laminate with the film having permeability can be made into a cloth-like complex material having very high water resistance and capable of making the best use of flexibility and stretchability of the spunbonded non-woven fabric of the present invention.

EXAMPLE

The present invention is described in more detail with reference to the following examples, but it should not be limited by them.

The physical properties in the examples and comparative examples were determined by the following methods.

(1) Basis Weight [g/m$^2$]

Six specimens having a size of 200 mm (machine direction: MD)×50 mm (crosswise direction: CD) were collected from a spunbonded non-woven fabric and/or a spunbonded non-woven fabric laminate. The specimens were collected in any 3 places in the MD direction or CD direction (total 6 places). Next, the mass (g) of each of the specimens was measured using an electronic even balance (manufactured by Kensei Co., Ltd.). The average of the masses of each specimen was determined. From the average, each mass was converted to the mass (g) per 1 m$^2$ and the value was rounded off the second decimal place and taken as the basis weight [g/m$^2$] of each non-woven fabric specimen.

(2) Maximum Strength [N/50 mm] and Maximum Point Elongation [%]

The measurement was carried out according to JIS L1906. Six specimens having a size of 200 mm (machine direction: MD)×50 mm (crosswise direction: CD) were collected from a spunbonded non-woven fabric and/or a spunbonded non-woven fabric laminate. The specimens were collected in any 3 places in the MD direction or CD direction (total 6 places). Next, each specimen was subjected to tensile test at a spun width IO of 100 mm at tensile rate of 100 mm/min using a universal tensile testing machine (IM-201 type, manufactured by Intesco Co., Ltd.). The maximum strength [N/50 mm] and the maximum point elongation [%] were determined. The maximum strength was determined by averaging the values on the 6 places (MD, CD each 3 places) and rounding the average off the second decimal place. The maximum point elongation was determined by averaging the values on the 6 places (MD, CD each 3 places) and rounding the average off the first decimal place.

(3) Stretching Properties (I)

The measurement was carried out using a universal tensile testing machine (IM-201 type, manufactured by Intesco Co., Ltd.). A specimen having a size of 200 mm (MD)×25 mm (CD) was collected from a spunbonded non-woven fabric and/or a spunbonded non-woven fabric laminate. The specimen was stretched by 100% in a sample width of 25 mm, in a chuck distance of 100 mm at a tensile rate of 300 mm/min and thereafter, the specimen was recovered until the original size at the same rate. This cycle was repeated twice. The value after the two cycle repetition (stress at the time of 50% stretching ($S_1$)÷stress at the time of 50% recovery ($S_2$)), namely, stress ratio ($S_1/S_2$) was determined and taken as the criterion of the stretching properties. When the stress ratio is smaller, the stretching properties are more excellent. The specimen was collected in any 3 places in the MD direction or CD direction and each average was determined and rounded off in the third decimal place. As the stress ratio, a higher value was used in each average value in the MD direction and the CD direction.

(4) Stretching Treatment

The measurement was carried out using a universal tensile testing machine (IM-201 type, manufactured by Intesco Co., Ltd.). A specimen having a size of 200 mm (MD)×25 mm (CD) was collected from a spunbonded non-woven fabric and/or a spunbonded non-woven fabric laminate. The specimen was stretched by 150% in a sample width of 25 mm, in a chuck distance of 100 mm at a tensile rate of 300 mm/min and thereafter, the specimen was recovered until the original size at the same rate.

(5) Stretching Properties (II)

The spunbonded non-woven fabric prepared by stretching treatment (stretchable spunbonded non-woven fabric) was evaluated in accordance with the measuring method of the stretching properties (I). The specimen was stretched by 100% in a sample width of 25 mm, in a chuck distance of 100 mm at a tensile rate of 300 mm/min and thereafter, the specimen was recovered until the original size at the same rate. After this cycle, the value (stress at the time of 50% stretching ($S_1$)÷stress at the time of 50% recovery ($S_2$)), namely, stress ratio ($S_1/S_2$) was determined and taken as the criterion of the stretching physical properties. When the stress ratio is smaller, the stretching properties are more excellent. The specimen was collected in any 3 places in the MD direction and CD direction and each average was determined and rounded off in the third decimal place. As the stress ratio, a higher value was used in each average value in the MD direction and the CD direction.

(6) Tackiness

Ten panelists touch on the spunbonded non-woven fabric and/or the spunbonded non-woven fabric laminate with their hands and evaluated the tackiness in the following criterion. Furthermore, the condition before (4) stretching treatment indicates before stretching treatment and the condition after measurement indicates after stretching treatment.

Very good: 10 panelists felt no tackiness and fine touch.
Good: 9 to 7 panelists of 10 panelists felt no tackiness and fine touch.
Somewhat good: 6 to 3 panelists of 10 panelists felt no tackiness and fine touch.
No good: 2 to 0 panelists of 10 panelists felt no tackiness and fine touch.

(7) Spinning Properties

The spinning condition around the nozzle surface of a device of producing the spunbonded non-woven fabric was observed visually. The number of fiber break per 5 min was counted (unit: times/5 min).

(8) Adhesion

In the device for producing the spunbonded non-woven fabric, the mixed fibers were deposited on a belt and derived for 5 min. When the web was passed through metal made nip rolls, the web adhesion condition was evaluated as the adhesion to rolls (I).

Good: Web adhesion was not confirmed at all visually.
Somewhat good: Web adhesion was not nearly confirmed visually.
No good: Web adhesion was confirmed visually, or the web was wound.

In the above method, when the mixed fibers were deposited on the belt and then derived for 10 min, the web condition was evaluated as the adhesion to rolls (2).

(9) Hardness

The hardness of TPU was measured using a type A durometer in accordance with JIS K-7311.

(10) Molecular Weight

The molecular weight of TPU was determined in the following manner. TPU was dissolved in a concentration of 0.4% by mass using a high-power GPC column (TSKgel GMHXL manufactured by Tohso Co., Ltd.) and measured in conditions that the sample injected amount was 100 μl and the flow rate of the elution THF was 1.0 ml/min using GPC device. From the resulting elution curve, the number average molecular weight (Mn), weight average molecular weight (Mw) and Mw/Mn were determined using polystyrene as a standard.

(11) Melt Viscosity

TPU was dried at 100° C. for 2 hr and about 2 g of a specimen was weighed. Using an elevated flow tester (manufactured by Shimadzu Corporation), the melt viscosity of the specimen was measured under a load of 30 kgf/cm$^2$ using a dice of 1 mm⌀×1 mml for a preheating time of 4 min at a measuring temperature of 200° C. (unit: $10^4$ dPa·s).

(12) Fluid Initiation Temperature

TPU was dried at 100° C. for 2 hr and about 2 g of a specimen was weighed. Using an elevated flow tester (manufactured by Shimadzu Corporation), the fluid initiation temperature of the specimen was measured under a load of 30 kgf/cm$^2$ using a dice of 1 mm⌀×1 mml for a preheating time of 10 min by increasing the temperature from 100° C. (unit: ° C.).

TPU Production Example 1

71.1 parts by weight of polyester polyol having a number average molecular weight of 1932, 4.8 parts by weight of 1,4-butane diol (hereinafter abbreviated to "BD"), 0.3 part by weight of pentaerythritol tetrakis[3-(3,5-di-t-butyl-4-hydroxyphenyl) propionate] (hereinafter abbreviated to "antioxidant-1") and 0.3 part by weight of polycarbone diimide were mixed. To the mixture, 22.9 parts by weight of MDI was added and mixed with highly stirring sufficiently and reacted at 160° C. for 1 hr. The reactant was pulverized. Thereafter, to 100 parts by weight of the pulverized matter, 0.2 part by weight of ethylene bisstearic acid amide, 0.5 part by weight of triethylene glycol-bis-[3-(3,5-di-t-butyl-4-hydroxyphenyl) propionate] (hereinafter abbreviated to "antioxidant-2"), 0.4 part by weight of ethylene bisoleic acid amide (hereinafter abbreviated to "EOA") and 0.8 part by weight of fine particles having an average particle diameter of 2.0 μm were mixed. Thereafter, the mixture was melt kneaded using an extruder at a set temperature of 210° C. and thereby granulated to prepare a thermoplastic polyurethane elastomer [TPU(A-1)].

The physical properties of TPU(A-1) were measured by the above methods. The results are shown in Table 1.

TPU Production Example 2

71.7 parts by weight of polyester polyol having a number average molecular weight of 1932, 4.8 parts by weight of BD, 0.3 part by weight of antioxidant-1 and 0.3 part by weight of polycarbone diimide were mixed. To the mixture, 22.9 parts by weight of MDI was added and mixed with highly stirring sufficiently and reacted at 160° C. for 1 hr. The reactant was pulverized. Thereafter, to 100 parts by weight of the pulverized matter, 0.8 part by weight of ethylene bisstearic acid amide, 0.5 part by weight of antioxidant-2 and 0.8 part by weight of EOA were mixed. Thereafter, the mixture was melt kneaded using an extruder at a set temperature of 210° C. and thereby granulated to prepare a thermoplastic polyurethane elastomer [TPU(A-2)].

The physical properties of TPU(A-2) were measured by the above methods. The results are shown in Table 1.

TPU Production Example 3

63.8 parts by weight of polyester polyol having a number average molecular weight of 1932, 7.3 parts by weight of BD, 0.3 part by weight of antioxidant-1 and 0.3 part by weight of polycarbone diimide were mixed. To the mixture, 28.3 parts by weight of MDI was added and mixed with highly stirring sufficiently and then reacted at 160° C. for 1 hr. The reactant was pulverized. Thereafter, to 100 parts by weight of the pulverized matter, 0.4 part by weight of ethylene bisstearic acid amide and 0.5 part by weight of antioxidant-2 were mixed. Thereafter, the mixture was melt kneaded using an extruder at a set temperature of 210° C. and thereby granulated to prepare a thermoplastic polyurethane elastomer [TPU(E-1)].

The physical properties of TPU(E-1) were measured by the above methods. The results are shown in Table 1.

TPU Production Example 4

71.7 parts by weight of polyester polyol having a number average molecular weight of 1932, 4.8 parts by weight of BD, 0.3 part by weight of antioxidant-1 and 0.3 part by weight of polycarbone diimide were mixed. To the mixture, 22.9 parts by weight of MDI was added and mixed with highly stirring sufficiently and then reacted at 160° C. for 1 hr. The reactant was pulverized. Thereafter, to 100 parts by weight of the pulverized matter, 0.4 part by weight of ethylene bisstearic acid amide and 0.5 part by weight of antioxidant-2 were mixed. Thereafter, the mixture was melt kneaded using an extruder at a set temperature of 210° C. and thereby granulated to prepare a thermoplastic polyurethane elastomer [TPU(E-2)].

The physical properties of TPU(E-2) were measured by the above methods. The results are shown in Table 1.

Example 1

Preparation of Thermoplastic Resin Composition for Spunbonded Non-Woven Fabric

96 Parts by weight of a propylene homopolymer having an MFR (measured in accordance with ASTM D1238 at 230° C.

under a load of 2.16 kg) of 60 g/10 min, a density of 0.91 g/cm³ and a melting point of 160° C. (hereinafter abbreviated to "PP-1") was mixed with 8 parts by weight of high density polyethylene having an MFR (measured in accordance with ASTM D1238 at 190° C. under a load of 2.16 kg) of 5 g/10 min, a density of 0.97 g/cm³ and a melting point of 134° C. (hereinafter abbreviated to "HDPE") to prepare a thermoplastic resin composition (B-1).

Production of Spunbonded Non-Woven Fabric

Each of TPU(A-1) and B-1 prepared in Production Example 1 was independently melted using an extruder of 75 mmØ and an extruder of 50 mmØ and then melt spun using a spunbonded non-woven fabric molding machine having a spinning port (length vertical to the machine flow direction on collecting surface: 800 mm) in such conditions that the resin temperature and the die temperature were each 205° C. and the cooling air temperature was 20° C. and the stretching air rate was 3200 m/min to deposit a web of the mixed long fibers formed from long fibers A of TPU(A-1) and long fibers B of B-1 on the collecting surface. The spinning port has a nozzle pattern such that output holes for TPU(A-1) and output holes for B-1 were arranged one after the other. The nozzle diameter for TPU(A-1) (fibers A) was 0.75 mmØ and the nozzle diameter for B-1 (fibers B) was 0.6 mmØ. The nozzle pitch in the vertical direction was 8 mm and the nozzle pitch in the horizontal direction was 11 mm, and the ratio of the nozzle number for fibers A to the nozzle number for fibers B was 1:1.45. The output amount of one hole for fibers A was 0.82 g/(min·hole) and the output amount of one hole for fibers B was 0.56 g/(min·hole).

The web of the mixed long fibers deposited was deposited on a moving belt and passed through between a metal made nip roll and a belt with a linear pressure of 15 kg/cm to prepare a mixed spunbonded non-woven fabric. The resulting mixed spunbonded non-woven fabric had a basis weight of 30 g/m². The web of the mixed long fibers deposited had a large fiber diameter of 27.1 μm and a small fiber diameter of 22.2 μm. In results, it was considered that the fiber diameter of TPU(A-1) was 27.1 μm and the fiber diameter of B-1 was 22.2 μm.

The web was released from the moving belt and subjected to heat embossing with an embossing pattern such that the area rate was 18% and the embossed area was 0.41 mm² at an average heating temperature of 95° C. at a linear pressure of 70 kg/cm to prepare a spunbonded non-woven fabric.

The resulting spunbonded non-woven fabric was evaluated by the above methods. The stretching properties (I) were measured using the spunbonded non-woven fabric prepared before stretching treatment, and the stretching properties (II) were measured using the spunbonded non-woven fabric prepared after stretching treatment namely using the stretchable spunbonded non-woven fabric. The evaluation results are shown in Table 1.

Example 2

The procedure of Example 1 was repeated except for using TPU(A-2) prepared in TPU production example 2 in place of TPU(A-1) used in Example 1 to prepare a spunbonded non-woven fabric. The resulting non-woven fabric was evaluated in the same methods as those of Example 1. The results are shown in Table 1.

Example 3

The procedure of Example 2 was repeated except that the individual hole output amount of fibers A was 0.60 g/min·hole and the individual hole output amount of fibers B was 0.61 g/min·hole to prepare a spunbonded non-woven fabric. The resulting non-woven fabric was evaluated in the same methods as those of Example 2. The results are shown in Table 1.

Example 4

The procedure of Example 2 was repeated except that the individual hole output amount of fibers A was 0.94 g/min·hole and the individual hole output amount of fibers B was 0.53 g/min·hole to prepare a spunbonded non-woven fabric. The resulting non-woven fabric was evaluated in the same methods as those of Example 2. The results are shown in Table 1.

Comparative Example 1

The procedure of Example 1 was repeated except for using TPU(E-1) prepared in TPU production example 3 in place of TPU(A-1) used in Example 1 to prepare a spunbonded non-woven fabric. In the case of judging the adhesion (I) as no good, molding of the non-woven fabric was carried out by winding a release paper to a metal made roll. The resulting non-woven fabric was evaluated in the same methods as those of Example 1. The results are shown in Table 1.

Comparative Example 2

The procedure of Comparative Example 1 was repeated except for using TPU(E-2) prepared in TPU production example 4 in place of TPU(E-1) used in Comparative Example 1 to prepare a spunbonded non-woven fabric. The resulting non-woven fabric was evaluated in the same methods as those of Comparative Example 1. The results are shown in Table 1.

Example 5

The procedure of Example 1 was repeated except for changing the individual hole output amount of fibers B into 0 g/min·hole, namely using only TPU(A-1) to prepare a spunbonded non-woven fabric. The spinning properties and adhesion (I) were evaluated as good. The resulting non-woven fabric had stretching properties (I) of 1.44 and had excellent stretchability.

Comparative Example 3

The procedure of Comparative Example 1 was repeated except that the individual hole output amount of fibers A was 0.60 g/min·hole and the individual hole output amount of fibers B was 0.61 g/min·hole to prepare a spunbonded non-woven fabric. The resulting non-woven fabric was evaluated in the same methods as those of Comparative Example 1.

The results are shown in Table 1.

Comparative Example 4

The procedure of Comparative Example 1 was repeated except that the individual hole output amount of fibers A was 0.94 g/min·hole and the individual hole output amount of fibers B was 0.53 g/min·hole to prepare a spunbonded non-woven fabric. The resulting non-woven fabric was evaluated in the same methods as those of Comparative Example 1.

The results are shown in Table 1.

TABLE 1

|  | Example 1 | Example 2 | Example 3 | Example 4 |
|---|---|---|---|---|
| TPU | | | | |
| Composition | A-1 | A-2 | A-2 | A-2 |
| Fiber weight ratio | 50% | 50% | 40% | 55% |
| Hardness | 81 | 81 | 81 | 81 |
| Molecular weight | 164824 | 152028 | 152028 | 152028 |
| EOA/fine particles | 0.4/0.8 | 0.8/— | 0.8/— | 0.8/— |
| Melt viscosity | 0.9 | 1.1 | 1.1 | 1.1 |
| Fluid initiation temperature | 156 | 155 | 155 | 155 |
| Evaluation | | | | |
| Basis weight | 30 | 30 | 30 | 30 |
| Maximum strength MD | 30.6 | 26.8 | 27.8 | 26.8 |
| Maximum strength CD | 12.9 | 10.5 | 12.0 | 10.7 |
| Maximum point elongation MD | 207 | 201 | 186 | 197 |
| Maximum point elongation CD | 225 | 211 | 200 | 214 |
| Spinning properties | Good | Good | Good | Good |
| Adhesion (1) | Good | Good | Good | Good |
| Adhesion (2) | No good | Good | Good | Good |
| Stretching properties I | 1.82 | 1.75 | 1.94 | 1.82 |
| Tackiness before stretching treatment | Good | Good | Good | Good |
| Stretching properties II | 1.70 | 1.64 | 1.88 | 1.71 |
| Tackiness after stretching treatment | Very good | Very good | Very good | Very good |

|  | Compar. Example 1 | Compar. Example 2 | Compar. Example 3 | Compar. Example 4 |
|---|---|---|---|---|
| TPU | | | | |
| Composition | E-1 | E-2 | E-1 | E-1 |
| Fiber weight ratio | 50% | 50% | 40% | 55% |
| Hardness | 87 | 82 | 87 | 87 |
| Molecular weight | 151515 | 170167 | 151515 | 151515 |
| EOA/fine particles | —/— | —/— | —/— | —/— |
| Melt viscosity | 1.1 | 1.4 | 1.1 | 1.1 |
| Fluid initiation temperature | 173 | 157 | 173 | 173 |
| Evaluation | | | | |
| Basis weight | 30 | 30 | 30 | 30 |
| Maximum strength MD | 24.1 | 29.7 | 28.0 | 26.0 |
| Maximum strength CD | 11.4 | 12.3 | 12.8 | 9.7 |
| Maximum point elongation MD | 171 | 200 | 151 | 180 |
| Maximum point elongation CD | 211 | 233 | 180 | 220 |
| Spinning properties | Good | Good | Good | Good |
| Adhesion (1) | No good | No good | No good | No good |
| Adhesion (2) | No good | No good | No good | No good |
| Stretching properties I | 1.98 | 1.82 | 2.21 | 1.86 |
| Tackiness before stretching treatment | Good | Somewhat good | Good | Good |
| Stretching properties II | 1.86 | 1.70 | 2.10 | 1.75 |
| Tackiness after stretching treatment | Very good | good | Very good | Very good |

TPU Production Example 5

73.8 parts by weight of polyester polyol having a number average molecular weight of 1932, 6.9 parts by weight of 1,4-bis(2-hydroxyethoxy)benzene (hereinafter abbreviated to "BHEB"), 0.3 part by weight of pentaerythritol tetrakis[3-(3,5-di-t-butyl-4-hydroxyphenyl)propionate] (hereinafter abbreviated to "antioxidant-1") and 0.3 part by weight of polycarbone diimide were mixed. To the mixture, 18.7 parts by weight of MDI was added and mixed with highly stirring sufficiently and then reacted at 160° C. for 1 hr. The reactant was pulverized. Thereafter, to 100 parts by weight of the pulverized matter, 0.2 part by weight of ethylene bisstearic acid amide, 0.5 part by weight of triethylene glycol-bis-[3-(3,5-di-t-butyl-4-hydroxyphenyl)propionate] (hereinafter abbreviated to "antioxidant-2"), 0.4 part by weight of ethylene bisoleic acid amide (hereinafter abbreviated to "EOA") and 0.8 part by weight of crosslinkedacryl fine particles having an average particle diameter of 2.0 μm (hereinafter abbreviated to "fine particles") were mixed. Thereafter, the mixture was melt kneaded using an extruder at a set temperature of 210° C. and thereby granulated to prepare a thermoplastic polyurethane elastomer [TPU(A2-1)].

The physical properties of TPU (A2-1) were measured by the above methods. The results are shown in Table 2.

TPU Production Example 6

72.3 parts by weight of polyester polyol having a number average molecular weight of 1932, 7.7 parts by weight of BHEB, 0.3 part by weight of antioxidant-1 and 0.3 part by weight of polycarbone diimide were mixed. To the mixture, 19.4 parts by weight of MDI was added and mixed with highly stirring sufficiently and then reacted at 160° C. for 1 hr. The reactant was pulverized. Thereafter, to 100 parts by weight of the pulverized matter, 0.2 part by weight of ethylene bisstearic acid amide, 0.5 part by weight of antioxidant-2, 0.4 part by weight of EOA and 0.8 part by weight of fine particles having an average particle diameter of 2.0 μm were mixed. Thereafter, the mixture was melt kneaded using an extruder at a set temperature of 210° C. and thereby granulated to prepare a thermoplastic polyurethane elastomer [TPU(A2-2)].

The physical properties of TPU (A2-2) were measured by the above methods. The results are shown in Table 2.

TPU Production Example 7

72.3 parts by weight of polyester polyol having a number average molecular weight of 1932, 7.7 parts by weight of BHEB, 0.3 part by weight of antioxidant-1 and 0.3 part by weight of polycarbone diimide were mixed. To the mixture, 19.4 parts by weight of MDI was added and mixed with highly stirring sufficiently and then reacted at 160° C. for 1 hr. The reactant was pulverized. Thereafter, to 100 parts by weight of the pulverized matter, 0.3 part by weight of ethylene bisstearic acid amide, 0.5 part by weight of antioxidant-2 and 0.4 part by weight of EOA were mixed. Thereafter, the mixture was melt kneaded using an extruder at a set temperature of 210° C. and thereby granulated to prepare a thermoplastic polyurethane elastomer [TPU(A2-3)].

The physical properties of TPU (A2-3) were measured by the above methods. The results are shown in Table 2.

TPU Production Example 8

72.3 parts by weight of polyester polyol having a number average molecular weight of 1932, 7.7 parts by weight of BHEB, 0.3 part by weight of antioxidant-1 and 0.3 part by weight of polycarbone diimide were mixed. To the mixture, 19.4 parts by weight of MDI was added and mixed with highly stirring sufficiently and then reacted at 160° C. for 1 hr. The reactant was pulverized. Thereafter, to 100 parts by weight of the pulverized matter, 0.8 part by weight of ethylene bisstearic acid amide, 0.5 part by weight of antioxidant-2 and 0.8 part by weight of EOA were mixed. Thereafter, the mixture was melt kneaded using an extruder at a set temperature of 210° C. and thereby granulated to prepare a thermoplastic polyurethane elastomer [TPU(A2-4)].

The physical properties of TPU (A2-4) were measured by the above methods. The results are shown in Table 2.

TPU Production Example 9

72.3 parts by weight of polyester polyol having a number average molecular weight of 1932, 7.7 parts by weight of BHEB, 0.3 part by weight of antioxidant-1 and 0.3 part by weight of polycarbone diimide were mixed. To the mixture, 19.4 parts by weight of MDI was added and mixed with highly stirring sufficiently and then reacted at 160° C. for 1 hr. The reactant was pulverized. Thereafter, to 100 parts by weight of the pulverized matter, 0.8 part by weight of ethylene bisstearic acid amide, 0.5 part by weight of antioxidant-2, 0.8 part by weight of EOA and 0.8 part by weight of fine particles having an average particle diameter of 2.0 μm were mixed. Thereafter, the mixture was melt kneaded using an extruder at a set temperature of 210° C. and thereby granulated to prepare a thermoplastic polyurethane elastomer [TPU(A2-5)].

The physical properties of TPU (A2-5) were measured by the above methods. The results are shown in Table 2.

TPU Production Example 10

72.3 parts by weight of polyester polyol having a number average molecular weight of 1932, 7.7 parts by weight of BHEB, 0.3 part by weight of antioxidant-1 and 0.3 part by weight of polycarbone diimide were mixed. To the mixture, 19.4 parts by weight of MDI was added and mixed with highly stirring sufficiently and then reacted at 160° C. for 1 hr. The reactant was pulverized. Thereafter, to 100 parts by weight of the pulverized matter, 0.2 part by weight of ethylene bisstearic acid amide and 0.5 part by weight of antioxidant-2 were mixed. Thereafter, the mixture was melt kneaded using an extruder at a set temperature of 210° C. and thereby granulated to prepare a thermoplastic polyurethane elastomer [TPU (D-1)].

The physical properties of TPU(D-1) were measured by the above methods. The results are shown in Table 3.

TPU Production Example 11

66.4 parts by weight of polyester polyol having a number average molecular weight of 1932, 10.4 parts by weight of BHEB, 0.3 part by weight of antioxidant-1 and 0.3 part by weight of polycarbone diimide were mixed. To the mixture, 22.6 parts by weight of MDI was added and mixed with highly stirring sufficiently and then reacted at 160° C. for 1 hr. The reactant was pulverized. Thereafter, to 100 parts by weight of the pulverized matter, 0.3 part by weight of ethylene bisstearic acid amide, 0.5 part by weight of antioxidant-2 and 0.4 part by weight of EOA were mixed. Thereafter, the mixture was melt kneaded using an extruder at a set temperature of 210° C. and thereby granulated to prepare a thermoplastic polyurethane elastomer [TPU(E-5)].

The physical properties of TPU(E-5) were measured by the above methods. The results are shown in Table 3.

Example 6

Preparation of Thermoplastic Resin Composition for Spunbonded Non-Woven Fabric

96 Parts by weight of a propylene homopolymer having an MFR (measured in accordance with ASTM D1238 at 230° C. under a load of 2.16 kg) of 60 g/10 min, a density of 0.91 g/cm$^3$ and a melting point of 160° C. (hereinafter abbreviated to "PP-1") was mixed with 8 parts by weight of high density polyethylene having an MFR (measured in accordance with ASTM D1238 at 190° C. under a load of 2.16 kg) of 5 g/10 min, a density of 0.97 g/cm$^3$ and a melting point of 134° C. (hereinafter abbreviated to "HDPE") to prepare a thermoplastic resin composition (B-1).

Production of Spunbonded Non-Woven Fabric

Each of TPU(A2-1) prepared in Production Example 5 and above B-1 was independently melted using an extruder of 75 mmØ and an extruder of 50 mmØ and then melt spun using a spunbonded non-woven fabric molding machine having a spinning port (length vertical to the machine flow direction on collecting surface: 800 mm) in such conditions that the resin temperature and the die temperature were each 205° C., the cooling air temperature was 20° C. and the stretching air rate was 3200 m/min to deposit a web of the mixed long fibers formed from long fibers A of TPU(A2-1) and long fibers B of B-1 on the collecting surface. The spinning port has a nozzle pattern such that output holes for TPU (A2-1) and an output holes for B-1 were arranged one after the other. The nozzle diameter of TPU(A2-1) (fibers A) was 0.75 mmØ and the nozzle diameter of B-1 (fibers B) was 0.6 mmØ. The nozzle pitch in the vertical direction was 8 mm and the nozzle pitch in the horizontal direction was 11 mm, and the ratio of the nozzle number for fibers A to the nozzle number for fibers B was 1:1.45. The output amount of one hole for fibers A was 0.82 g/(min·hole) and the output amount of one hole for fibers B was 0.56 g/(min·hole).

The web of the mixed long fibers deposited was deposited on a moving belt and passed through between a metal made nip roll and a belt with a linear pressure of 15 kg/cm to prepare a mixed spunbonded non-woven fabric. The resulting mixed spunbonded non-woven fabric had a basis weight of 30 g/m$^2$. The web of the mixed long fibers deposited had a large fiber diameter of 27.1 μm and a small fiber diameter of 22.2 μm. In results, it was considered that the fiber diameter of TPU(A2-1) was 27.1 μm and the fiber diameter of B-1 was 22.2 μm.

The web was released from the moving belt and subjected to heat embossing with an embossing pattern such that the area rate was 18% and the embossed area was 0.41 mm$^2$ at an average heating temperature of 85° C. at a linear pressure of 70 kg/cm to prepare a spunbonded non-woven fabric.

The resulting spunbonded non-woven fabric was evaluated by the above methods. The stretching properties (I) were measured using the spunbonded non-woven fabric prepared before stretching treatment, and the stretching properties (II) were measured using the spunbonded non-woven fabric prepared after stretching treatment namely using the stretchable spunbonded non-woven fabric. The evaluation results are shown in Table 2.

Example 7

The procedure of Example 6 was repeated except for using TPU(A2-2) prepared in TPU production example 6 in place of TPU(A2-1) used in Example 6 to prepare a spunbonded non-woven fabric. The resulting non-woven fabric was evaluated in the same methods as those of Example 6.

The results are shown in Table 2.

Example 8

The procedure of Example 6 was repeated except for using TPU(A2-3) prepared in TPU production example 7 in place of TPU(A2-1) used in Example 6 to prepare a spunbonded non-woven fabric. The resulting non-woven fabric was evaluated in the same methods as those of Example 6.

The results are shown in Table 2.

Example 9

The procedure of Example 6 was repeated except for using TPU(A2-4) prepared in TPU production example 8 in place of TPU(A2-1) used in Example 6 to prepare a spunbonded non-woven fabric. The resulting non-woven fabric was evaluated in the same methods as those of Example 6.

The results are shown in Table 2.

Example 10

The procedure of Example 6 was repeated except that TPU(A2-3) prepared in TPU production example 7 was used in place of TPU(A2-1) used in Example 6, the individual hole output amount of fibers A was 0.60 g/min·hole and the individual hole output amount of fibers B was 0.61 g/min·hole to prepare a spunbonded non-woven fabric. The resulting non-woven fabric was evaluated in the same methods as those of Example 6.

The results are shown in Table 2.

Example 11

The procedure of Example 6 was repeated except that TPU(A2-5) prepared in TPU production example 9 was used in place of TPU(A2-1) used in Example 6, the individual hole output amount of fibers A was 0.94 g/min. hole and the individual hole output amount of fibers B was 0.53 g/min. hole to prepare a spunbonded non-woven fabric. The resulting non-woven fabric was evaluated in the same methods as those of Example 6.

The results are shown in Table 2.

Comparative Example 5

The procedure of Example 6 was repeated except for using TPU(D-1) prepared in TPU production example 10 in place of TPU(A2-1) used in Example 6 to prepare a spunbonded non-woven fabric. In the case of judging the adhesion (II) as no good, molding of the non-woven fabric was carried out by winding a release paper to a metal made roll. The resulting non-woven fabric was evaluated in the same methods as those of Example 6. The results are shown in Table 3.

Comparative Example 6

The procedure of Comparative Example 5 was repeated except for using TPU(E-5) prepared in TPU production example 11 in place of TPU(D-1) used in Comparative Example 5 to prepare a spunbonded non-woven fabric. The resulting non-woven fabric was evaluated in the same methods as those of Comparative Example 5. The results are shown in Table 3.

Example 12

The procedure of Example 1 was repeated except that the individual hole output amount of fibers B was 0 g/min·hole to prepare a spunbonded non-woven fabric only formed from TPU (A2-1). The resulting non-woven fabric was evaluated with the result that the spinning properties, the adhesion (1) and the adhesion (2) were good. Furthermore, the stretching properties (I) were 1.44 and the stretchability was excellent.

TABLE 2

|  | Ex. 6 | Ex. 7 | Ex. 8 | Ex. 9 | Ex. 10 | Ex. 11 |
|---|---|---|---|---|---|---|
| TPU | | | | | | |
| Composition | A2-1 | A2-2 | A2-3 | A2-4 | A2-3 | A2-5 |
| Fiber weight ratio | 50% | 50% | 50% | 50% | 40% | 55% |
| Hardness | 80 | 83 | 82 | 83 | 82 | 83 |
| Molecular weight | 153555 | 168483 | 126421 | 121053 | 126421 | 160882 |
| EOA/fine particles | 0.4/0.8 | 0.4/0.8 | 0.4/— | 0.8/— | 0.4/— | 0.8/0.8 |
| Melt viscosity | 0.4 | 0.8 | 0.4 | 0.5 | 0.4 | 1.3 |
| Fluid initiation temperature | 162 | 170 | 168 | 168 | 168 | 164 |
| Evaluation | | | | | | |
| Basis weight | 30 | 30 | 30 | 30 | 30 | 30 |
| Maximum strength MD | 25.6 | 29.6 | 24.5 | 25.6 | 27.8 | 26.8 |
| Maximum strength CD | 10.1 | 12.5 | 10.0 | 10.1 | 12.0 | 10.7 |
| Maximum point elongation MD | 206 | 201 | 200 | 187 | 186 | 197 |
| Maximum point elongation CD | 218 | 200 | 225 | 208 | 200 | 214 |
| Spinning properties | Good | Good | Good | Good | Good | Good |
| Adhesion (1) | Good | Good | Good | Good | Good | Good |
| Adhesion (2) | Good | Good | Good | Good | Good | Good |
| Stretching properties I | 1.71 | 1.54 | 1.64 | 1.70 | 1.77 | 1.60 |
| Tackiness before stretching treatment | Good | Good | Good | Good | Good | Good |
| Stretching properties II | 1.60 | 1.44 | 1.53 | 1.59 | 1.66 | 1.51 |
| Tackiness after stretching treatment | Very good | Very good | Very good | Very good | Very good | Very good |

TABLE 3

|  | Compar. Ex. 5 | Compar. Ex. 6 |
|---|---|---|
| TPU | | |
| Composition | D-1 | E-5 |
| Fiber weight ratio | 50% | 50% |
| Hardness | 83 | 87 |
| Molecular weight | 195408 | 92743 |
| EOA/fine particles | —/— | 0.4/— |
| Melt viscosity | 1.1 | 1.7 |
| Fluid initiation temperature | 171 | 173 |
| Evaluation | | |
| Basis weight | 30 | 30 |
| Maximum strength MD | 26.3 | Failure for evaluation |
| Maximum strength CD | 11.3 | Failure for evaluation |
| Maximum point elongation MD | 188 | Failure for evaluation |
| Maximum point elongation CD | 205 | Failure for evaluation |
| Spinning properties | Good | No good |
| Adhesion (1) | No good | Failure for evaluation |
| Adhesion (2) | No good | Failure for evaluation |
| Stretching properties I | 1.64 | Failure for evaluation |
| Tackiness before stretching treatment | Somewhat good | Failure for evaluation |
| Stretching properties II | 1.53 | — |
| Tackiness after stretching treatment | Good | — |

POSSIBILITY FOR INDUSTRIAL USE

The spunbonded non-woven fabric of the present invention comprises the long fibers of the thermoplastic polyurethane elastomer having a relatively low hardness and has high stretching physical properties, good touch and fuzz resistance. The spunbonded non-woven fabric of the present invention is suitably used for sanitary materials such as paper diapers and the like.

DESCRIPTION OF NUMERALS

1: Gear roll of gear stretching device
2: Spunbonded non-woven fabric

The invention claimed is:

1. A spunbonded non-woven fabric comprising continuous fibers which comprise a thermoplastic polyurethane elastomer (A) containing ethylene bisoleic acid amide and having a hardness of 75 to 85.

2. The spunbonded non-woven fabric according to claim 1 further comprising continuous fibers which comprise a thermoplastic resin (B) other than the thermoplastic polyurethane elastomer (A).

3. The spunbonded non-woven fabric according to claim 2 wherein the continuous fibers which comprise the thermoplastic resin (B) are non-stretchable fibers.

4. The spunbonded non-woven fabric according to claim 2 which comprises 10 to 90% by mass of the continuos fibers of the thermoplastic polyurethane elastomer (A) and 90 to 10% by mass of the continuos fibers of the thermoplastic resin (B).

5. The spunbonded non-woven fabric according to claim 2 wherein the thermoplastic resin (B) is a polymer containing polyethylene and/or polypropylene.

6. The spunbonded non-woven fabric according to claim 1 wherein the thermoplastic polyurethane elastomer (A) is a thermoplastic polyurethane elastomer (A2) obtained by using 1,4-bis(2-hydroxyethoxy)benzene as a chain extender.

7. The spunbonded non-woven fabric according to claim 1 wherein the thermoplastic polyurethane elastomer (A) has a fluid initiation temperature of not lower than 155° C.

8. The spunbonded non-woven fabric according to claim 6 wherein the thermoplastic polyurethane elastomer (A2) has a fluid initiation temperature of not lower than 160° C.

9. A stretchable spunbonded non-woven fabric obtainable by stretching and processing a spunbonded non-woven fabric as claimed in claim 1.

10. A laminate comprising at least one layer which comprises a stretchable spunbonded non-woven fabric as claimed in claim 9.

11. A sanitary material comprising a stretchable spunbonded non-woven fabric as claimed in claim 9.

12. The spunbonded non-woven fabric according to claim 1 further comprising crosslinked organic fine particles.

* * * * *